(12) United States Patent
Kempen

(10) Patent No.: US 6,859,280 B2
(45) Date of Patent: *Feb. 22, 2005

(54) IMAGING APPARATUS AND METHOD

(75) Inventor: Lothar U. Kempen, Redondo Beach, CA (US)

(73) Assignee: Maven Technologies LLC, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/602,555

(22) Filed: Jun. 23, 2003

(65) Prior Publication Data

US 2004/0051871 A1 Mar. 18, 2004

Related U.S. Application Data

(63) Continuation of application No. 09/614,503, filed on Jul. 11, 2000, now Pat. No. 6,594,011.

(51) Int. Cl.[7] .......................... G01J 4/00; G01N 33/557
(52) U.S. Cl. ....................... 356/369; 356/445; 436/517; 436/805
(58) Field of Search ................................ 356/364–369, 356/128, 136, 445, 446; 422/82.08, 11, 82; 435/6, 7.1, 288.7, 808; 436/517, 805, 527

(56) References Cited

U.S. PATENT DOCUMENTS

| 4,238,565 | A |   | 12/1980 | Hornby et al. |
| 4,256,834 | A |   | 3/1981  | Zuk et al. |
| 4,508,832 | A | * | 4/1985  | Carter et al. ................. 436/517 |
| 5,164,589 | A |   | 11/1992 | Sjoedin |
| 5,229,833 | A | * | 7/1993  | Stewart ....................... 356/364 |

(List continued on next page.)

FOREIGN PATENT DOCUMENTS

| AU | 742417        | 2/2000  |
| WO | WO 96/08720   | 3/1996  |
| WO | WO 96/38729   | 12/1996 |
| WO | WO 97/19375   | 5/1997  |
| WO | WO 98/32002   | 7/1998  |
| WO | WO 03/056337 A1 | 7/2003 |
| WO | WO 03/102580 A1 | 12/2003 |

OTHER PUBLICATIONS

Tadashi Saitoh, et al. "Optical Characterization of Very Thin Hydrogenated Amorphous Silicon Films Using Spectroscopic Ellipsometry"; Japanese Journal of Applied Physics; vol. 30, No. 118, Nov. 1991, pp. L1914–L1916.

"Handbook of Optics", Michael Bass Editor in Chief, by The Optical Society of America; vol. 1; pp. 4.23, 4.24; 1995 McGraw–Hill, Inc.

Bass, et al. "Handbook of Optics", by The Optical Society of America; vol. 1; Section 41.10; 1995 McGraw–Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930–2936, Aug. 1996.

Max Born et al. "Principles of Optics—Electromagnetic Theory of Propagation Interference and Diffraction of Light", Sixth Edition, pp. 47–51 Pergamon Press.

(List continued on next page.)

*Primary Examiner*—Hoa Q. Pham
(74) *Attorney, Agent, or Firm*—MacPherson Kwok Chen & Heid LLP; David S. Park

(57) ABSTRACT

Imaging apparatus and method which uses change of polarization state of a light beam passed through a total internal reflection structure by a single reflection at a TIR surface in which a specimen is placed in the evanescent field associated with the total internal reflection of the light beam, the specimen being the subject of biological, chemical or genetic investigation.

33 Claims, 2 Drawing Sheets

U.S. PATENT DOCUMENTS

| | | | | |
|---|---|---|---|---|
| 5,255,075 A | * | 10/1993 | Cush | 356/445 |
| 5,313,264 A | | 5/1994 | Ivarsson et al. | |
| 5,437,840 A | * | 8/1995 | King et al. | 422/82.08 |
| 5,483,346 A | * | 1/1996 | Butzer | 356/369 |
| 5,485,277 A | * | 1/1996 | Foster | 356/445 |
| 5,491,556 A | * | 2/1996 | Stewart et al. | 356/445 |
| 5,573,956 A | | 11/1996 | Hanning | |
| 5,593,130 A | | 1/1997 | Hansson et al. | |
| 5,633,724 A | * | 5/1997 | King et al. | 356/445 |
| 5,641,640 A | | 6/1997 | Hanning | |
| RE35,716 E | | 1/1998 | Stapleton et al. | |
| 5,753,518 A | | 5/1998 | Karlsson | |
| 5,856,873 A | * | 1/1999 | Naya et al. | 356/369 |
| 5,922,594 A | | 7/1999 | Loefas | |
| 5,922,604 A | | 7/1999 | Stapleton et al. | |
| 5,955,729 A | | 9/1999 | Nelson et al. | |
| 5,965,456 A | | 10/1999 | Malmqvist et al. | |
| 5,972,612 A | | 10/1999 | Malmqvist et al. | |
| 6,008,010 A | | 12/1999 | Greenberger et al. | |
| 6,008,893 A | | 12/1999 | Roos et al. | |
| 6,045,996 A | | 4/2000 | Cronin et al. | |
| 6,127,183 A | | 10/2000 | Ivarsson et al. | |
| 6,140,044 A | | 10/2000 | Bessemer et al. | |
| 6,143,513 A | | 11/2000 | Loefas | |
| 6,143,574 A | | 11/2000 | Karlsson et al. | |
| 6,197,595 B1 | | 3/2001 | Anderson et al. | |
| 6,200,814 B1 | | 3/2001 | Malmqvist et al. | |
| 6,207,381 B1 | | 3/2001 | Larsson et al. | |
| 6,277,330 B1 | | 8/2001 | Liu et al. | |
| 6,289,286 B1 | | 9/2001 | Andersson et al. | |
| 6,493,097 B1 | | 12/2002 | Ivarsson | |
| 6,503,760 B2 | | 1/2003 | Malmqvist et al. | |
| D472,644 S | | 4/2003 | Dawson et al. | |
| 6,589,798 B1 | | 7/2003 | Loefas | |
| 6,594,011 B1 | * | 7/2003 | Kempen | 356/369 |
| D480,149 S | | 9/2003 | Dawson et al. | |
| 6,698,454 B2 | | 3/2004 | Sjoelander et al. | |
| 2002/0019019 A1 | | 2/2002 | Hamalainen et al. | |
| 2002/0154311 A1 | | 10/2002 | Ivarsson | |
| 2002/0182717 A1 | | 12/2002 | Karlsson | |
| 2003/0022388 A1 | | 1/2003 | Roos et al. | |
| 2003/0067612 A1 | | 4/2003 | Ivarsson | |
| 2004/0002167 A1 | | 1/2004 | Andersson et al. | |
| 2004/0012676 A1 | | 1/2004 | Weiner et al. | |
| 2004/0023247 A1 | | 2/2004 | Xu et al. | |
| 2004/0030504 A1 | | 2/2004 | Helt et al. | |
| 2004/0038268 A1 | | 2/2004 | Pirrung et al. | |

OTHER PUBLICATIONS

Eggins, "Biosensors: An Introduction", pp. 112–113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3–4 pp. 439–449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7–D13, Papers No. 232–496 pp. 509–512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44–50, 1992.

Ulf Jonsson et al. "Flow–Injection Ellipsometry—An in Situ Method for the Study of Biomolecular Adsorption and Interaction at Solid Surfaces," Colloids and Surfaces, 13 (1985) pp. 333–339, 1985 Elsevier Science Publishers BV, Amsterdam, The Netherlands.

Jonsson, Ulf et al. "Biosensors Based on Surface Concentration Measuring Devices–The Concept of Surface Concentration" Progress in Colloid and Polymer Sci. vol. 70, pp. 96–100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International, Inc., Sunnyvale, California, USA, A BioTechniques Books Publication, Easton Publishing, pp. 10–11, 2000.

Harland G. Tompkins, et al. "Spectroscopic Ellipsometry and Reflectometry A User's Guide" A Wiley–Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381–1351, 1988 Academic Press, Inc. Harcourt Brace Jovanovich, Publishers.

CH Striebel et al. "Characterization of Biomembranes by Spectral Ellipsometry, Surface Plasmon Resonance and Interferometry with Regard to Biosensor Application", Biosensors & Bioelectronics 9, pp. 139–146, 1994 Elsevier Science Publishers Ltd.

T.A. Ruzgas et al. "Ellipsometric Immunosensors for the Determination of γ–Interferon and Human Serum Albumin", Biosensors & Bioelectronics 7, pp. 305–308, 1992 Elsevier Science Publsihers Ltd.

Haken Nygren et al. "Determination by Ellipsometry of the Affinity of Monoclonal Antibodies", Journal of Immunological Methods, 92, pp. 219–225, 1986 Elsevier Science Publishers Ltd.

John F. Place et al. "Opto–electronic Immunosensors: A Review of Optical Immunoessay At Continuous Surfaces", Biosensors 1, pp. 321–353, 1985 Elsevier Applied Science Publishers Ltd., England.

A. Brecht et al. "Biosensors: Fundamentals, Technologies and Applications" GBF Monographs, vol. 17, pp. 174–178, 1991 Germany.

Hakan Nygren et al. "Kinetics of Antibody–Binding to Surface–Immobilized Antigen: Influence of Mass Transport on the Enzyme–Linked Immunosorbent Assay (ELISA)", Journal of Colloid and Interface Science, vol. 107, No. 2 pp. 560–566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70–78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81–91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163–181, 1995 Humana Press Inc.

G. Elender et al. "Wetting and Dewetting of Si/SiO2–Wafers by Free and Lipid–Monolayer Covered Aqueous Solutions Under Controlled Humidity", Journal de Physique, II France 4 pp. 455–479, Mar. 1994.

C.F. Mandenius et al. "Coupling of Biomolecules to Silicon Surfaces for use in ellipsometry and other related techniques", Methods in Enzymology, vol. 137, pp. 389–394, 1988 Academic Press, Inc.

A.W. Flounders et al. "Patterning of immobilized antibody layers via photolithography and oxygen plasma exposure", Biosensors and Bioelectronics, vol. 12, No. 6 pp. 447–456, 1997 Elsevier Science Ltd., Great Britain.

A. Ahluwalia et al. "A comparative study of protein immobilization techniques for optical immunosensors", Biosensors and Bioelectronics 7, (1991) pp. 207–214, 1992 Elsevier Science Publishers Ltd.

Dr. Rudolf Oldenbourg "Metamorph Imaging System", http://www.image1.com/products/metapotscope/ Universal Imaging Corporation Last Updated Jun. 10, 1999 pp. 1–2.

Dr. Rudolf Oldenbourg "A new view on polarization microscopy", Nature, vol. 381, pp. 811–812, Jun. 27, 1996.

Clifford C. Hoyt et al. "Structural analysis with quantitative birefringence imaging", American Laboratory, pp. 34–42, Jul. 1999.

Dirk Honig et al. "Direct visualization of monolayers at the air–water interface by Brewster angle microscopy", J. Phys. Chem., pp. 4590 & 4592, 1991 American Chemical Society.

S. Henon et al. "Microscope at the Brewster angle: direct observation of first–order phase transitions in monolayers", Rev. Sci. Instrum. 62, (4) pp. 936–939, Apr. 1991 American Institute of Physics.

Gang Jin et al. "A biosensor concept based on imaging ellipsometry for visualization of biomolecular interactions", Analytical Biochemistry 232, pp. 69–72, 1995.

Pentti Tengvall et al. "Complement activation by 3–mercapto–1,2–propanediol immobilized on gold surfaces", Biomaterials vol. 17, No. 10 pp. 1001–1007, 1995 Elsevier Science Ltd., Great Britain.

H. Arwin "Spectroscopic ellipsometry and biology: recent developments and challenges", Thin Solid Films 313–314, pp. 7640774, 1998 Elsevier Science S.A.

Christopher Palmer "Diffraction Grating Handbook", pp. 35–44, 2000 Richardson Grating Laboratory, Rochester, New York.

Erwin G. Loewen "Diffraction Gratings, Ruled and Holographic", Applied Optics and Optical Engineering, vol. IX, pp. 33–71, Bausch and Lomb, Inc., Rochester, New York 1983 Academic Press, Inc.

* cited by examiner

IMAGING APPARATUS AND METHOD

RELATED APPLICATION

This application is a continuation of U.S. application Ser. No. 09/614,503 filed Jul. 11, 2000. now U.S. Pat. No. 6,594,011, the contents of which are incorporated by reference herein for all purposes.

FIELD OF THE INVENTION

This invention relates to imaging techniques in conjunction with total infernal reflection at the boundary of an optically transparent material and more particularly to the use of such techniques for detecting the presence, composition, quantity, and spatial distribution of substances on optically transparent substrates.

BACKGROUND OF THE INVENTION

It is well known that the presence or the properties of substances on a material's surface can be determined by light-based sensors. Polarization-based techniques are particularly sensitive; ellipsometry, for example, is a widely used technique for surface analysis and has successfully been employed for detecting attachment of proteins and smaller molecules to a surface. In U.S. Pat. No. 4,508,832 to Carter, et al. (1985), an ellipsometer is employed to measure antibody-antigen attachment in an immunoassay on a test surface. Recently, imaging ellipsometry has been demonstrated, using a light source to illuminate an entire surface and employing a two-dimensional array for detection, thus measuring the surface properties for each point of the entire surface in parallel(G. Jin, R. Janson and H. Arwin, "Imaging Ellipsometry Revisited: Developments for Visualization of Thin Transparent Layers on Silicon Substrates," Review of Scientific Instruments, 67(8), 2930–2936, 1996). Imaging methods are advantageous in contrast to methods performing multiple single-point measurements using a scanning method, because the status of each point of the surface is acquired simultaneously, whereas the scanning process takes a considerable amount of time (for example, some minutes), and creates a time lag between individual point measurements. For performing measurements where dynamic changes of the surface properties occur in different locations, a time lag between measurements makes it difficult or impossible to acquire the status of the entire surface at any given time. Reported applications of imaging ellipsometry were performed on a silicon surface, with the light employed for the measurement passing through+the surrounding medium, either air or a liquid contained in a cuvette. For applications where the optical properties of the surrounding medium can change during the measurement process, passing light through the medium is disadvantageous because it introduces a disturbance of the measurement.

By using an optically transparent substrate, this problem can be overcome using the principle of total internal reflection (TIR), where both the illuminating light and the reflected light pass through the substrate. In TIR, the light interacting with the substance on the surface is confined to a very thin region above the surface, the so-called evanescent field. This provides a very high contrast readout, because influences of the surrounding medium are considerably reduced. In U.S. Pat. No. 5,483,346 to Butzer, (1996) the use of polarization for detecting and analyzing substances on a transparent material's surface using TIR is described. In the system described by Butzer, however, the light undergoes multiple internal reflections before being analyzed, making it difficult or impossible to perform an imaging technique, because it cannot distinguish which of the multiple reflections caused the local polarization change detected in the respective parts of the emerging light beam. U.S. Pat. No. 5,633,724 to King, et al. (1997) describes the readout of a biochemical array using the evanescent field. This patent focuses on fluorescent assays, using the evanescent field to excite fluorescent markers attached to the substances to be detected and analyzed. The attachment of fluorescent markers or other molecular tags to the substances to be detected on the surface requires an additional step in performing the measurement, which is not required in the current invention. The patent further describes use of a resonant cavity to provide on an evanescent field for exciting analytes.

SUMMARY OF THE INVENTION

In accordance with the principles of this invention, light from a light source member providing an extended, polarized light beam is directed through a transparent substrate and undergoes total internal reflection at the surface of the substrate by a single reflection within the TIR member. The reflected light is detected by a polarization-sensitive, two-dimensional array detector. The changes of the local polarization state in the beam's cross-section caused by the total internal reflection are employed to obtain information about the presence and composition in an array of substances on the substrate surface for each point of the surface. Total internal reflection is described in; M. Born, et al., "Principles of Optics", $6^{th}$ ed., pp 47–51, Pergamon Press, Oxford, 1991. In accordance with one aspect of the invention, the light generating element within the light source member is a quasi-monochromatic light source of moderate bandwidth. In a preferred embodiment, the light generating element within the light source member is an LED of moderate bandwidth. The light from the light source member is directed through an internal reflection member to reflect off a specimen. The total internal reflection at any point within the cross-section of the light beam causes a phase shift between the light component polarized in the plane of incidence and the component polarized perpendicular to the plane of incidence. The reflected light is detected by a polarization-sensitive, two dimensional array detector and the signal from this detector is then processed in a computer to provide two-dimensional information about substances on the surface of the specimen. Spatially distributed changes in polarization state in the cross-section of the reflected beam are indicative of the substances in the specimen in the location in the specimen array corresponding to a position in the detector. The apparatus and method is especially adapted for imaging material in an aqueous solution. It is furthermore particularly suited for detecting attachment and detachment of analytes to a two-dimensional biomolecular array positioned on the total internal reflection member as part of a biosensor system. In various applications a plurality of discrete specimen spots are presented in an array, where the method and apparatus will image the array so as to distinguish each of the discrete specimen spots by an image which represents the change in polarization state within each of the discrete specimen spots. Fluorescence or molecular tagging is not necessary nor practical for use in this invention.

BRIEF DESCRIPTION OF DRAWINGS

FIG. 3 is a block diagram of alternative portions of the invention.

FIG. 4 is a block diagram of alternative portions of the invention.

FIG. 5 is a block diagram of alternative portions of the invention.

DETAILED DESCRIPTION

Figure 1:
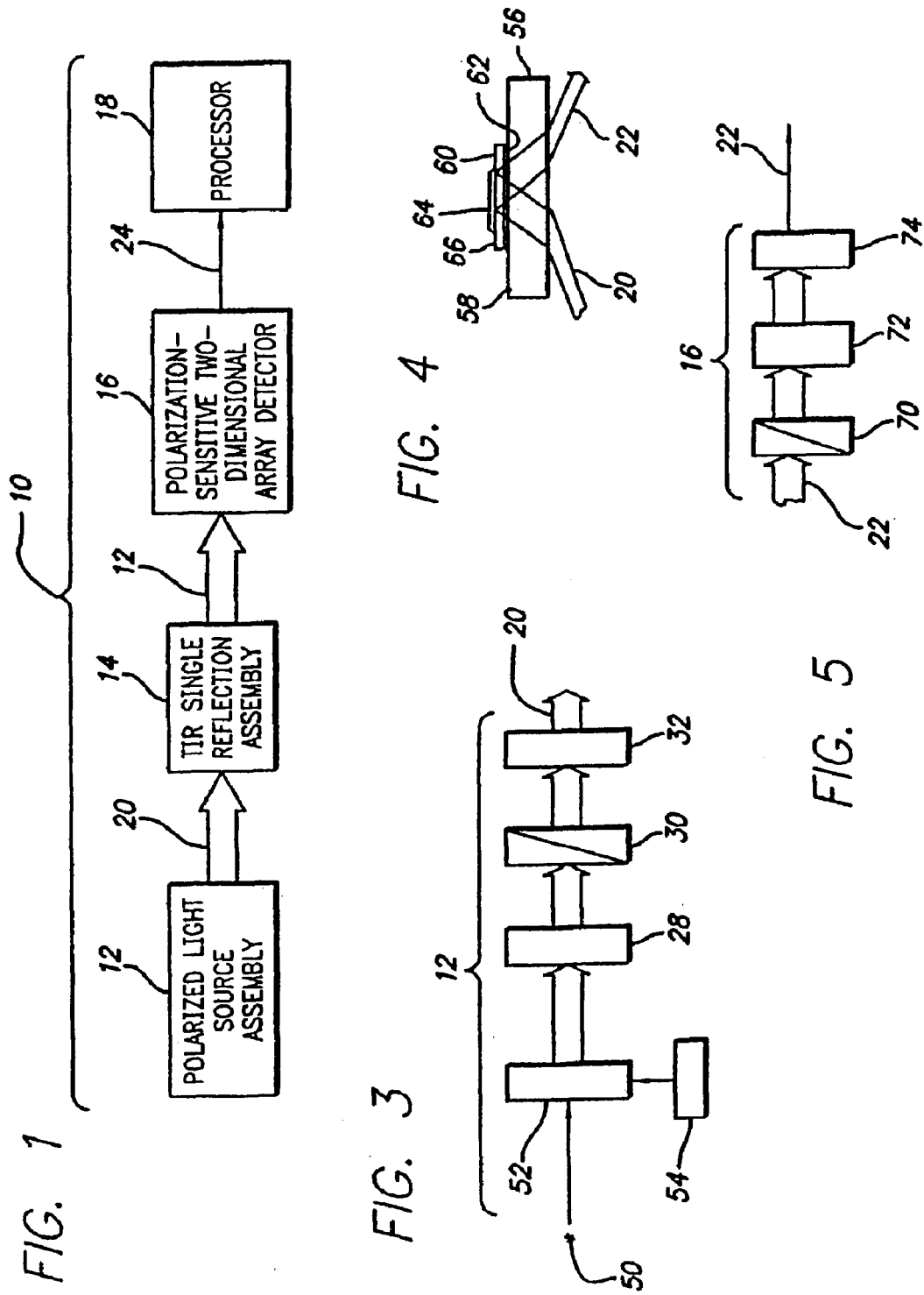
FIG. 1 is a block diagram of the invention.

The invention comprises a method and apparatus for analyzing a two-dimensional arrangement of chemical substances with an imaging technique. A polarized light source of known polarization state is directed into a total internal reflection member (TIR member) configured for a single reflection at a total internal reflection surface (TIR surface) and then exiting the TIR member. In the context of this document, superposition of reflections as encountered at a layered optical structure where the layer thicknesses are smaller than the coherence length of the illuminating light is referred to as a single reflection. The chemical specimen is in place above the TIR surface in the evanescent field of the reflected light beam. After reflection, the beam is passed to a polarization-sensitive two-dimensional detector such as a polarizer and a camera. The beam's content can then be processed to determine the change in polarization state, locally in the two-dimensional cross-section of the beam. This provides a spatially distributed map of change of polarization state in the specimen. A variety of techniques is available to determine the change in polarization such as measuring the deviation from a null condition or by comparing the input polarization state to the output polarization state.

The refractive index composition of the materials within the evanescent field determines the change in the polarization state of the beam due to the reflection at the TIR surface. A two-dimensional variation of this composition within the TIR surface is associated with a respective variation of the polarization state spatially distributed across the cross-section of the reflected light beam.

In one application, the chemical specimen forms a two-dimensional array of molecules (here referred to as receptors) with specific affinities towards respective other molecules (here referred to a ligands). In this application, the invention is utilized to indicate the presence or absence of binding between ligands and receptors on the array. Such arrays commonly consist of a plurality of discrete specimen spots. The present method and apparatus will image the array so as to distinguish each of the discrete specimen spots represented by the local change in polarization state in the cross-section of the reflected beam.

Subject to limitations in resolving power of the detector, the invention permits measurement of thickness and/or refractive index composition of the specimen under investigation with a very high resolution, in the sub angstrom range, spatially resolved over an entire area. The invention is particularly useful in applications where the specimen is in an aqueous solution. In a particular application, the present invention is used to determine the presence of biological agents in a solution such as in immunosensor applications by measuring their attachment to antibodies on the TIR surface in the evanescent field. In another application, the present invention is used to determine the presence and structure of nucleic acid sequences in a solution by measuring their attachment to other nucleic acid sequences on the TIR surface in the evanescent field. Described in more detail below are different embodiments of the invention.

Figure 2:
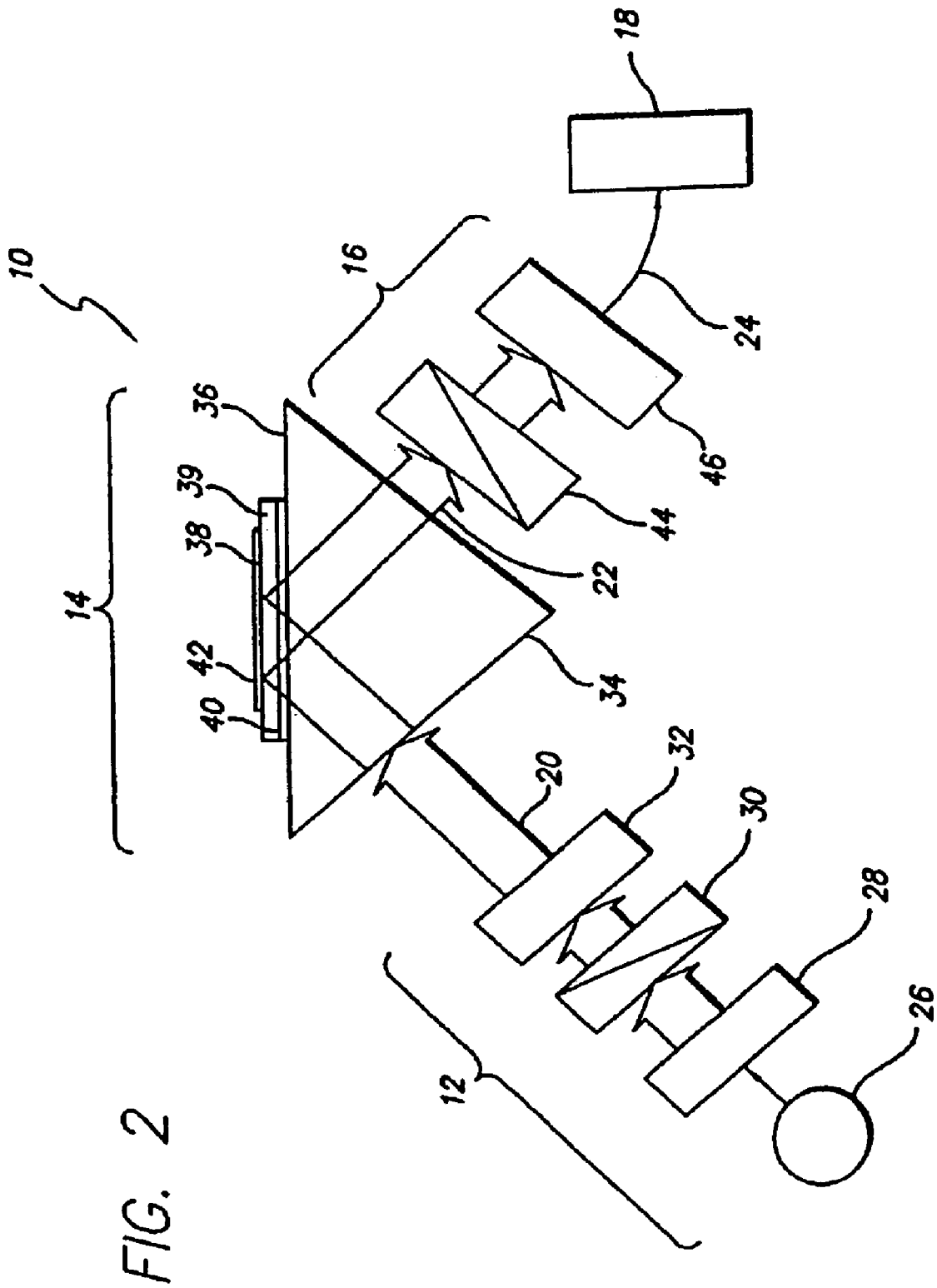
FIG. 2 is a block diagram of an embodiment of the invention.

Referring to FIGS. 1 and 2, an apparatus and method is illustrated which implements one embodiment of the invention. As shown in FIG. 1, the apparatus 10 can be conveniently described as consisting of three general portions. Portion 12 is a polarized light source assembly, portion 14 is a total internal reflection assembly and portion 16 is a polarization-sensitive two-dimensional array detector assembly. Data from the detector assembly 16 is sent by an electrical signal 24 to processor 18 such as a specially programmed computer and user access system such as a print-out or image display. Data can be presented as an image, a data table, or in other forms. The polarized light source assembly 12 passes polarized light of known polarization state (which may be varied or varying) 20 to the total internal reflection assembly 14 and the reflected light 22 having a changed polarization state passes to the detector assembly 16, where it is recorded spatially over the cross-section of the beam. The recorded data is sent to the processor 18 where the change of polarization state is determined to provide a spatially resolved map of changes in polarization state. Where the specimens are presented as an array of discrete spots, each spot will be imaged for its change in polarization state within the spot area.

FIG. 2 shows a more detailed preferred embodiment. The polarized light source assembly 12 has a light source 26, a beam forming member 28 (if the nature of the light source is such as to make beam forming useful or necessary) a polarizer 30 and an optical retarder 32. The total internal light reflection assembly 14 has a an optical element 34 which has an optical surface 36. Also shown is a specimen slide 38 on the optical surface 36, and between them an index-matching substance 40. Because of the index matching a total internal reflection surface (TIR surface) is defined as the upper surface 39 of the specimen slide 38. A specimen 42 is on the total internal reflection surface 39 of the slide 38. The optical element 34 is a prism configured along with the index matched slide 38 in relationship to the incoming light beam 20, and the exiting light beam 22 such that the beam reflects only a single time at the TIR surface 39 and then exits the prism. If the specimen is placed directly on the optical surface 36, then the optical surface 36 would be the TIR surface. But this is not the usual application as the specimen (such as a biochip) is usually prepared more conveniently on a specimen slide 38 and placed in the apparatus. In any event, however constructed, there is an optical structure having a TIR surface and the beam reflects only a single time at the TIR surface between entering and leaving the optical structure. In other words, there is a TIR surface in optical contact with the specimen, such that the evanescent field associated with the total internal reflection interacts with the specimen, and there is only a single reflection at that TIR surface.

The post reflection detector assembly 16 has a polarizer 44, and a two-dimensional array detector 46, preferably a camera of the CCD type. The processor 18 is a specially programmed computer and output means for processing the imagery into a representation of film thickness variations spatially resolved over the cross-section of the area imaged. The imaging is acquired by detecting changes spatially distributed in the local polarization state in the beam's cross-section caused by the total internal reflection. This provides information about the presence and composition in the array of substances on the substrate surface for each resolvable point on the surface. Different polarization state changes are included in the cross-section of the reflected beam indicative of the substances on the specimen in the location in the specimen array corresponding to a position in the detector. The processor 18 receives the data as an electrical signal 24 and characterizes the change of polarization state spatially over the two-dimensional array. In the processor 18, the analysis and processing is done in one embodiment by comparing the known polarization state of the incoming light from the light processing assembly 12 with the changed polarization state of the reflected light 22, spatially resolved two-dimensionally within the beam which provides a map of spatially distributed points or spots in the specimen array. The polarization shift is then analyzed by the processor 18 to provide information of the presence and properties of elements in the chemical specimen. Other known techniques, such as null processing can be used to determine the change in polarization state.

Alternatively, the light source member 26 may be an LED, an SLD (Super Luminescent Diode), an incandescent light source, or a laser. If an LED or SLD is used, the set-up shown in FIG. 2 is appropriate, where the beam forming member 28 is a collimator. If an incandescent light source is used, an optical filter is also used.

In one embodiment, the light source 26 for the apparatus is a quasi-monochromatic light source of moderate bandwidth. In accordance with the invention the light source 26 is preferably an LED of moderate bandwidth. Preferably the bandwidth is a full width half maximum wavelength in the range of about 10 nm–50 nm, and more preferably a full width half maximum wavelength in the range of about 30 nm–50 nm.

Referring to the optical retarder 32 as shown in FIG. 2, in an alternative embodiment, the optical retarder could be placed instead in the exiting beam path 22 before the polarizer 44.

Referring to FIG. 3, an alternative embodiment is shown. When the light source is a laser 50, a moving diffuser 52 is adapted to produce speckle offsetting fluctuation of the minima and maxima in the speckle pattern caused by the laser. The moving diffuser 52 is attached to a mechanical actuator 54 which is preferably a motor and servo-apparatus for providing the speckle offsetting fluctuations. The beam 20 then proceeds through the beam forming element 28, the polarizer 30 and the optical retarder 32, exiting the light source assembly 20.

The polarizer 30 employs a polarizer of selected known polarization state. The polarizer 30 may be of the type having a mechanical actuator driven by a motor control signal so as to enable varying and selecting the polarization state of the light beam 20.

As mentioned above, the total internal reflection optical element 34 either alone or in combination with an index matched slide may be arranged for use with a specimen in various ways to define a total internal reflection assembly so long as the specimen is in the evanescent field of the reflected beam 20, 22.

As noted above, the specimen 42 could be set directly on the optical surface 36 in which case the optical surface 36 would be the TIR surface but this is inconvenient and repeated use is likely to degrade the optical quality of the optical surface 36, and therefore, consistent with common practice in which a biochip or other chemical assay specimen is provided, a specimen slide 38 or other supporting apparatus is employed. It is common in a biochip to provide an array of discrete specimen spots supported on a structure for obtaining analysis of each spot. The term total internal reflection optical element refers to known optical elements alone or in combination with other elements which provide the phenomenon known as total internal reflection. FIG. 2 shows use of a prism combined with a slide 38, being index matched so that there is a TIR surface 39.

FIG. 4 shows an alternative optical arrangement in which a flat optical member 56 having an upper surface 58 is surmounted by a specimen slide 60 and an index matching substance 62 on which is a specimen 64. The TIR surface 66 is the top of the slide 60. The beam 20 enters the assembly, is refracted as it enters, and leaves the optical member 56 after a single reflection at the TIR surface 66 as beam 22. Other mechanisms for providing total internal reflection and an evanescent field can be employed in practicing this invention as long as only a single reflection occurs at the TIR surface upon which the specimen is placed so as to be in the evanescent field associated with the reflection.

As seen in FIG. 5, the post-reflection processing arrangement 16 through which the beam 22 passes, can alternatively, consist of a polarizer member 70, a beam forming member 72 and a two-dimensional array detector 74.

The method and apparatus can be used in combination with biochips of the type having discrete specimen spots or a micro-titer plate containing an array of discrete spots or locations for analysis, where the detected change in polarization state is spatially related to the discrete locations in the reflected beam. Therefore, as used herein the slide and specimen refers to any type of chemical or biological array which is desired to be examined.

The foregoing described apparatus and methods are especially beneficial for imaging materials in an aqueous medium.

Although particular embodiments of the invention have been described and illustrated herein, it is recognized that modifications and variations may readily occur to those skilled in the art, and consequently it is intended that the claims be interpreted to cover such modifications and equivalents.

What is claimed is:

1. An apparatus for imaging, comprising:
    a light source emitting a polarized light beam;
    a structure having a surface, the light beam from the light source being reflected by the surface to provide an evanescent field, and the surface being adapted to allow placing thereon a specimen array such that the specimen array in the evanescent field causes spatially distributed polarization changes in the cross-section of the light beam; and
    a two-dimensional array detector positioned to detect the spatially distributed polarization changes caused by the specimen army.

2. The apparatus as in claim 1, wherein the light source comprises a quasi-monochromatic light source of moderate bandwidth.

3. The apparatus as in claim 2, wherein the quasi-monochromatic light source of moderate bandwidth is a light-emitting diode (LED).

4. The apparatus as claim 2, wherein the quasi-monochromatic light source of moderate bandwidth is a superluminoscent diode (SLD).

5. The apparatus as in claim 2, wherein the quasi-monochromatic light source of moderate bandwidth has an optical bandwidth with a full width half maximum between 5 nm and 60 nm.

6. The apparatus as in claim 2, wherein the quasi-monochromatic light source of moderate bandwidth comprises an incandescent source and an optical filter, the light emitted from the incandescent source passing through the optical filters the optical filter limiting the wavelengths of the light transmitted through the optical filter such as to constitute quasi-monochromatic light of moderate bandwidth.

7. The apparatus as in claim 1, wherein the light source comprises a laser emitting substantially coherent light, and further comprising an optical diffuser mechanically attached to a mechanical actuator, the light emitted from the laser passing through the diffuser, the diffuser being moved with respect to the laser by the actuator, the movement of the diffuser with respect to the laser creating fluctuations in the speckle pattern of light detected by the detector, the fluctuations being adapted to remove speckle effects from the light detected by the detector.

8. The apparatus as in claim 7, wherein the mechanical actuator is a motor rotating the optical diffuser.

9. The apparatus as in claim 1, wherein the light source comprises a beam forming system, the beam forming system causing the light emerging from the light source to be collimated.

10. The apparatus as in claim 1, wherein the light source comprises an optical polarizer.

11. The apparatus as in claim 1, wherein the light source comprises an optical retarder, the retarder introducing an optical phase shift between two orthogonal components of light passing through the retarder.

12. The apparatus as in claim 11, wherein the optical retarder is controllably rotated by a motor.

13. The apparatus as in claim 11, wherein the optical retarder changes retardance according to an externally introduced physical parameter.

14. The apparatus as in claim 1, wherein the structure comprises an optical prism.

15. The apparatus as in claim 14, wherein the light beam from the light source is directed to enter the optical prism along an axis perpendicular to one of the sides of the optical prism.

16. The apparatus as in claim 14, wherein the light reflected from the surface exits the optical prism along an axis perpendicular to one of the sides of the optical prism.

17. The apparatus as in claim 1, wherein the specimen array comprises a two-dimensional array formed of multiple fields comprising biomolecular substances.

18. The apparatus as in claim 17, wherein the biomolecular substances are proteins.

19. The apparatus as in claim 17, wherein the biomolecular substances are peptides.

20. The apparatus as in claim 17, wherein the biomoleculer substances are polynucleotide sequences.

21. The apparatus as in claim 1, wherein the two-dimensional array detector comprises an optical polarizer.

22. The apparatus as in claim 21, wherein the optical polarizer is controllably rotated by a motor.

23. The apparatus as in claim 1, wherein the two-dimensional array detector comprises a two-dimensional CCD array.

24. The apparatus as in claim 1, wherein the two-dimensional array detector comprises a two-dimensional photodiode array.

25. The apparatus as in claim 1, further comprising a signal processing member connected to the two-dimensional array detector, the signal processing member processing the signal from the two-dimensional array detector to obtain a two-dimensional representation of the optical phase shifts occurring in the specimen array.

26. A method of imaging, comprising:

passing a polarized light beam into an optical structure for reflection at a surface of the optical structure to provide an evanescent field, a specimen array in the evanescent field causing spatially distributed polarization changes in the cross-section of the light beam;

passing the reflected light beam out of the optical structure;

detecting the spatially distributed polarization changes caused by the specimen array; and processing the detected spatially distributed polarization changes to provide an image of the specimen array.

27. The method of claim 26, wherein the specimen array comprises a plurality of discrete specimen spots and the image is provided for each of the discrete specimen spots.

28. The method of claim 26, further comprising using the spatially distributed polarization changes to determine two-dimensionally distributed presence and/or properties of the specimen array constituents.

29. The method of claim 28, wherein the specimen array is in a micro-titer plate.

30. The method of claim 29, further comprising:

resolving the spatially distributed polarization changes for matching positions in the micro-titer plate; and analyzing the polarization changes to determine desired characteristics in each position.

31. The method of claim 26, wherein the specimen array is a series of discrete specimen spots.

32. The method of claim 31, further comprising analyzing the polarization changes to determine the binding characteristics of each discrete specimen spot.

33. The method of claim 26, wherein a specimen array having no molecular tagging is pieced in the evanescent field.

* * * * *

UNITED STATES PATENT AND TRADEMARK OFFICE
CERTIFICATE OF CORRECTION

PATENT NO. : 6,859,280 B2
DATED : February 22, 2005
INVENTOR(S) : Lothar U. Kempen It is certified that error appears in the above-identified patent and that said Letters Patent is hereby corrected as shown below:

Column 1,
Line 11, delete "infernal" and insert -- internal --.

Signed and Sealed this

Eighteenth Day of October, 2005

JON W. DUDAS
*Director of the United States Patent and Trademark Office*